United States Patent [19]
Saadat et al.

[11] Patent Number: 4,766,324
[45] Date of Patent: Aug. 23, 1988

[54] PARTICLE DETECTION METHOD INCLUDING COMPARISON BETWEEN SEQUENTIAL SCANS

[75] Inventors: Soheil Saadat, Sunnyvale; Jiri Pecen; Armand P. Neukermans, both of Palo Alto; George J. Kren, Los Altos, all of Calif.

[73] Assignee: Tencor Instruments, Mountain View, Calif.

[21] Appl. No.: 83,695

[22] Filed: Aug. 7, 1987

[51] Int. Cl.⁴ .............................................. G01N 21/00
[52] U.S. Cl. ..................................... 250/563; 356/431
[58] Field of Search ............... 250/562, 563, 572, 571; 356/237, 429–431, 446; 364/550, 555; 358/106

[56] References Cited

U.S. PATENT DOCUMENTS

| 4,378,159 | 3/1983 | Galbraith | 356/237 |
| 4,541,011 | 9/1985 | Mayer et al. | 250/563 |
| 4,681,442 | 7/1987 | Wagner | 250/563 |

OTHER PUBLICATIONS

Tullis, Barclay J., "A Method of Measuring and Specifying Particle Contamination by Process Equipment", Microcontamination, Nov. 1985–Jan., 1986, three parts.
Gise, Peter, "Applications of Laser Scanning for Wafer and Photoplate Inspection" Microcontamination, Oct.-/Nov., 1983, pp. 41–44 and 62.
Gise, Peter, "Principles of Laser Scanning for Defect and Contamination Detection in Microfabrication," Solid State Technology, Nov., 1983, pp. 163–165.

*Primary Examiner*—David C. Nelms
*Assistant Examiner*—Charles Wieland
*Attorney, Agent, or Firm*—Thomas Schneck

[57] ABSTRACT

A particle detection method for matching particles detected in two scans of a surface taken at different times in which particles having a light scattering intensity above a collection threshold are first detected and the measured position and scattering intensity therefor stored in a computer memory. Corresponding first and second measured positions from the respective first and second scans are determined by forming a triangle from selected first detected particles and finding those second detected particles which form a variant triangle with matching perimeter and area. From these matching first and second particles a transformation is found for mapping first measured positions to corresponding second positions and vice versa. Areas around corresponding positions of particles having a scattering intensity above a display threshold are examined for matching particles. If not found, the area is reexamined at a reduced threshold. Matching particles are considered to be the same, while unmatched particles are considered to be either added or removed. The method provides an accurate count of particles for process contamination analysis.

19 Claims, 4 Drawing Sheets

PARTICLE DETECTION METHOD INCLUDING COMPARISON BETWEEN SEQUENTIAL SCANS

TECHNICAL FIELD

The present invention relates to the optical measuring and testing of surfaces for the presence of particles in order to obtain their number, distribution and size, and also to the processing of particle detection data, particularly data obtained by light scattering from particles into a detector.

BACKGROUND ART

Laser scanning devices have been developed to detect particles, dust and other contamination, as well as defects, such as scratches, cracks, pits and the like, on surfaces, especially silicon wafer substrates and photoplates. Typically, these devices operate by detecting surface scattered light in a detector, such as a photomultiplier tube. One common use for these instruments is to determine the level of contamination caused by specific pieces of process equipment. A wafer substrate or other surface is first examined in a particle detector and the number of particles larger than a predetermined critical size is counted. Next, the wafer is sent through the piece of process equipment being tested and exposed to the process. After processing, the wafer substrate surface is again examined and the number of particles thereon is counted. The hope is that the difference in the two numbers obtained, one before processing and one after processing, will represent the total number of particles added by the process equipment, so that the level of contamination by each specific piece of equipment can be quantified.

Laser scanning particle detectors only detect those particles on a surface which when illuminated produce a level of scattered light such that the scattered light intensity received and measured by the photodetector is above a certain threshold intensity. Through this threshold set in the instrument, which may be a machine threshold at the limits of particle detectability or more usually a higher user specified threshold, the particle count is determined. Unfortunately, the measured light scattering intensity for any particular particle tends to vary from scan to scan due to variations in the way a particle is illuminated, nonuniformities in the light collection system, photon statistics, optical background noise, and other causes. Particles having an average measured light scattering intensity that is near threshold may or may not be detected in any given scan, depending on whether or not the actual measured light scattering intensity is above or below threshold. Detection of particles is done with a finite probability, and therefore different scans of the same wafer will likely give different particle counts. The problem is exacerbated when the user specified threshold is near the machine threshold, since photon statistics and optical background noise tend to be relatively large compared to the low levels of scattered light from very small particles. One solution might appear to be to average a large number of counts. However, in a production environment where time is valuable, it would be desirable to have a particle detection method that produces acceptably accurate counts in only a few scans.

Referring again to the process equipment testing application for particle detectors, it is often desirable to indicate not only the number of particles added by a piece of equipment but also their spatial distribution. In order to determine which particles have been added, previous systems have determined the positions of the detected particles for each measurement with reference to a coordinate system based upon the shape of a wafer. Unfortunately, determination of particle positions with respect to the wafer edge is imprecise and in some cases can cause poor correspondence between the two measurements. Apparatus for accurately positioning and aligning wafers abound. However, these can be quite complex and costly and may significantly add to the measurement time of a wafer. It would be desirable to have a method that enables the wafer surface to be examined in any position and orientation and compared with other surface examinations.

Further complicating the comparison of two particle measurements at different times is the random nature of particle detection for particles near threshold. When comparing two measurements, a particle seen in the second scan but not in the first may have been added by the process equipment, but alternately may have been present on the wafer during the first scan with a light scattering intensity below threshold. It would be desirable to be able to distinguish these two cases so that only added particles are displayed and likewise for those particles removed.

An object of the present invention is to produce a particle detection method that results in acceptable accurate particle counts in only a few scans, even for user selected thresholds corresponding to very small particles.

Another object of the invention is to produce a particle detection method which is capable of comparing two particle scans taken at different wafer orientations and positions, and which can distinguish between particles added or removed from the surface and particles present during both scans but not detected in one of the scans.

DISCLOSURE OF THE INVENTION

The above objects have been met with a method in which particles on a surface detected at first and second times are matched, i.e. identified as being the same particle, or identified as having been either added or removed, by first calculating a transformation for mapping measured positions of particles detected at one time onto corresponding positions on the surface at the other time, then examining areas around each of the corresponding positions for particles. Only those particles whose measured light scattering intensities are above a user specified display threshold intensity are checked for matching particles. However, unlike prior methods, particles are detected at first and second times and the position and scattering intensity information is stored in a computer memory for all particles having a light scattering intensity greater than a collection threshold intensity, where the collection threshold is less than the display threshold. If for any particle being checked, a matching particle with a scattering intensity above the display threshold is not found in the corresponding area, the corresponding area is reexamined at a reduced threshold lower than the display threshold by a predetermined amount. A particle in the reexamined area with a scattering intensity greater than the reduced threshold is considered to be the same as the particle being checked. If no particle is found, the particle being checked is considered to have been removed or added, depending on whether the particle being checked was detected at the first or second time. Thus, by looking under the display threshold, added or removed particles are distinguished from other particles and accurate particle counts and a count of added and removed particles are obtainable in only a few scans.

More generally, events detected by an instrument during one set of measurements are matched to events at corresponding locations detected during another set of measurements, or are determined to be either new or old. Events for which a measured parameter exceeds a collection threshold are collected, but only those events for which the parameter exceeds a display threshold are examined. If a matching event is not found at the corresponding location, the location is reexamined at a reduced threshold. Any unmatched events are either new, i.e. added, or old, i.e. removed. The results may be counted or displayed by event locations.

In order to identify corresponding first and second measured positions, a mapping technique may be used. The technique relies only on inter-particle distances, and not on the position of particles relative to a flat edge or fixed point of the wafer. Three or more particles detected at the first time with scattering intensities that are substantially above a threshold intensity may be selected from computer memory. The selected particles define a polygon, such as a triangle, with a characteristic perimeter and area. For each of these selected particles, candidates are selected from the set of particles detected at the second time. Each candidate particle has a light scattering intensity within a predetermined range of intensities around the scattering intensity of the selected particle for which it is a candidate. From these candidate particles, variants of the first polygon are formed. Candidate particles forming the variant polygon determined to have a perimeter and area closest to that of the first polygon are identified as being the same as the selected particles forming the first polygon so long as areas and perimeters are within a desired percent, i.e. 0.1% of each other. From the measured positions of these three or more pairs of same particles, transformations may be calculated which map measured positions of particles detected at one time to measured positions of particles detected at the other time. By applying the transformation to each of the measured positions of particles, corresponding positions are obtained for the above described area examinations. Thus, good correspondence between two scans is achieved for wafers in any position or orientation.

BEST MODE FOR CARRYING OUT THE INVENTION

Figure 1:
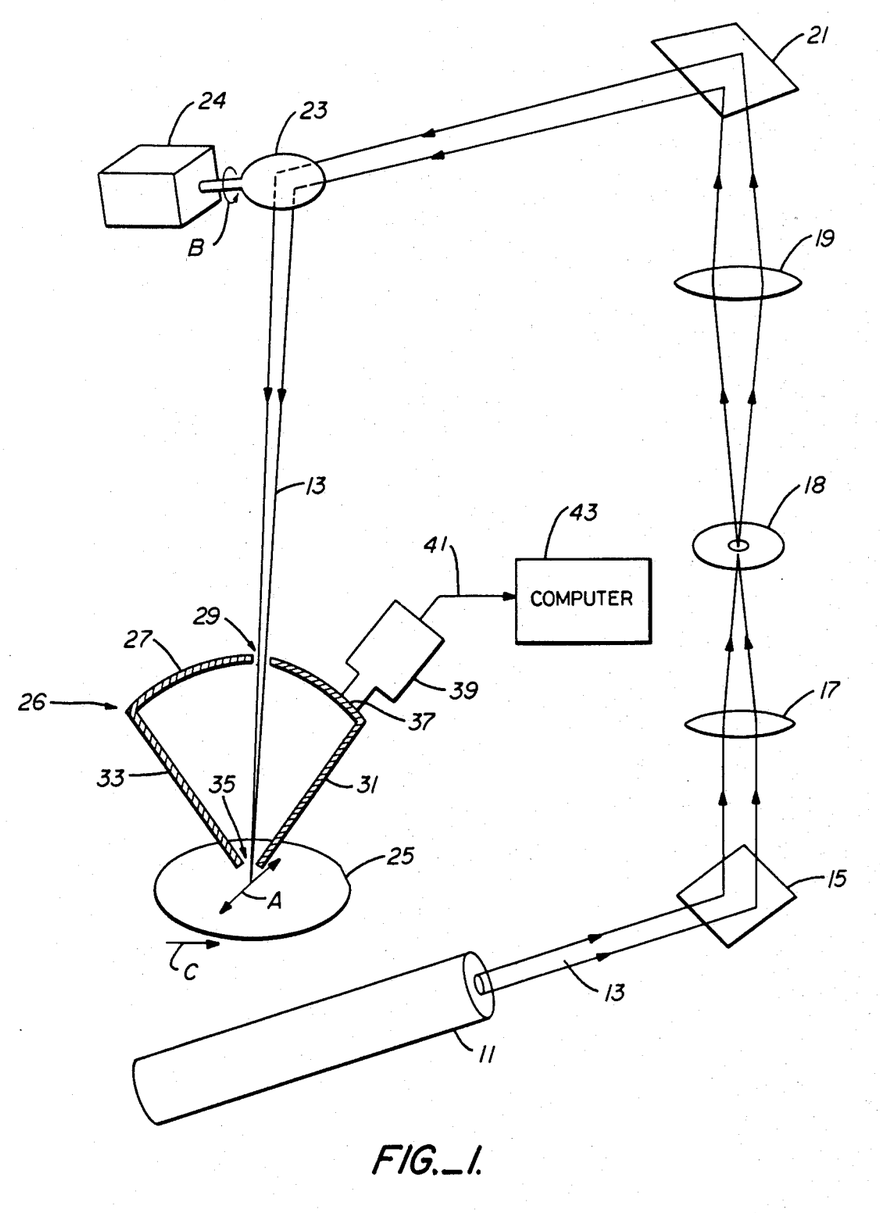
FIG. 1 is a simplified schematic view of a laser scanning particle detection apparatus carrying out the method of the present invention.

With reference to FIG. 1, a laser scanning particle detection apparatus has a laser 11 directing a beam 13 toward mirror 15. Typically, laser 11 is a low power helium-neon general purpose laser having an output of about 2 milliwatts. Other lasers may also be used. Beam 13 is directed to a focusing lens 17 and then to a beam collimating and focusing lens 19. A spatial filter 18 a short distance from lens 17 allows only the central portion of the beam to proceed. The focal length of lens 19 is approximately 14 cm. From lens 19 the beam is directed toward a fixed mirror 21 and then to a galvanometer mirror 23. A galvanometer coil 24 causes mirror 23 to oscillate. The system of lenses 17 and 19, filter 18 and mirrors 21 and 23 focuses the laser light into a converging beam 13 focused in a 100 μm spot in the plane of a wafer 25. The focal length of lens 19 is long enough so that the beam stays in focus and a fine beam spot is maintained as the beam is swept across the surface 25, even though the beam 13 makes a slightly arcuate trajectory. The beam is swept rapidly across the wafer 25 in the direction indicated by arrows A by the mirror 23 oscillating in the direction indicated by arrows B, while the wafer 25 moves at a constant speed on a belt track or the like in the direction indicated by arrow C. The result is a raster scan of the entire wafer surface.

Light scattered from particles or defects in the scan path on the wafer surface is collected by a light collector 26. Light collector 26 may comprise a sector 27 of a spherical shell with a reflective inside surface, and mirror surfaces 31 and 33 which form a V-shaped trough in which shell 27 rests. Shell 27 has a slit 29 through which beam 13 enters, and specularly reflected light exits. The beam passes through an exit aperture 35, opposite slit 29, between the bottom edges of mirror surfaces 31 and 33. This type of light collector intercepts and integrates the light scattered over a range of about 0° to about ±45° from the incoming beam direction, and directs the light through a detector port 37 to a photomultiplier tube 39 or other light detector.

The output of photomultiplier tube 39 is connected to a comparator which also receives a predetermined reference signal corresponding to a collection threshold intensity. The collection threshold intensity and other threshold intensities disclosed in this application are typically based on the mean intensity of scattered light measured by the photomultiplier tube 39 from a particle of a particular size. The reference signal may also be adjusted to compensate for ambient light pickup, changes in laser output, and photomultiplier aging. Any detector signal which is above the reference signal level causes the comparator to produce an output signal 41 representing the measured scattered light intensity from a particular point on the wafer.

Position information and the light scattering intensity information from output signal 41 is stored in the memory of a computer 43. As previously mentioned, the light beam 13 sweeps the wafer 25 in the direction indicated by arrows A. The beam position is known because the position of the galvanometer mirror 23 is known. The galvanometer mirror provides a Y-direction address for the beam. Further, the wafer 25 moves in a direction indicated by arrow C transverse to the Y-direction sweep by the beam at a known rate. This motion provides an X-direction address. The addresses are used in a random access memory in computer 43 to provide addresses for scattering intensities observed by the detector and provided by signal 41. Computer 43 analyzes the data stored in its memory according to the method to be described below to provide a count of particles taken at two times and to provide a count of particles added or removed during the interval between the two times.

Figure 2:
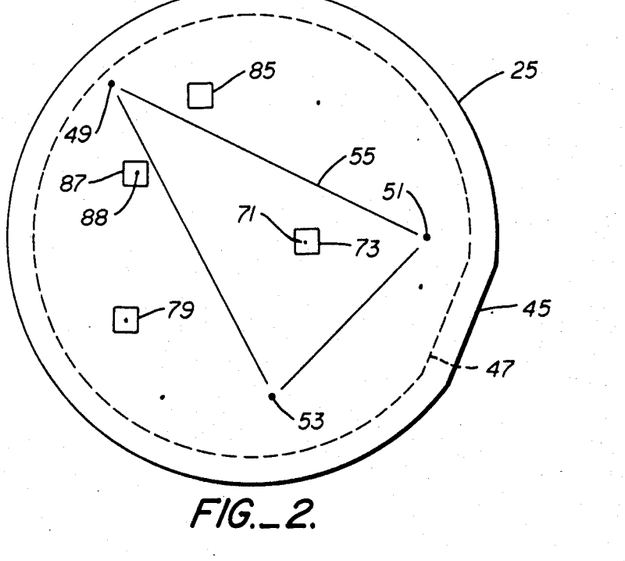
FIGS. 2 and 3 are top plan views of wafers inspected at respective first and second times by the apparatus of FIG. 1.
Figure 3:
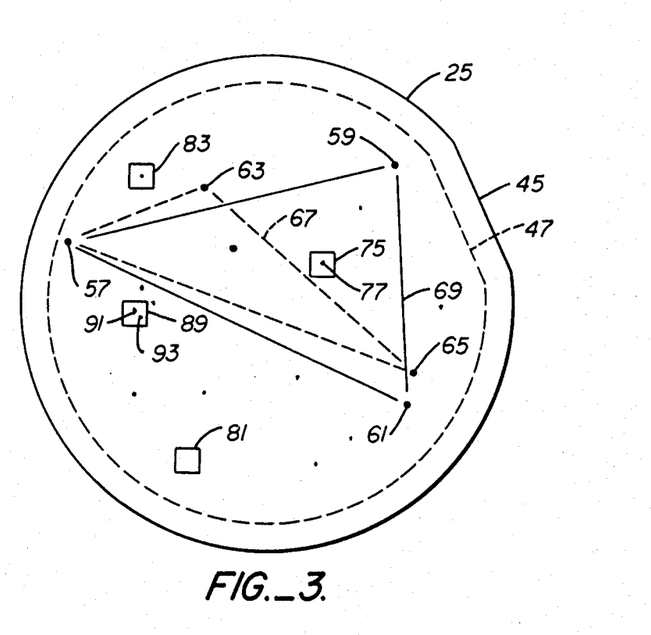

With reference to FIGS. 2 and 3, wafer 25 is scanned by a laser scanning particle detection apparatus, like that shown in FIG. 1 at first and second times, respectively. Typically wafer 25 has one or more flat regions 45 for wafer alignment and orientation. However, the method of the present invention is capable of obtaining good correspondence between measurements at different times regardless of the wafer's alignment and orientation. First and second times may be closely spaced, as for example, two particle counting measurements made one after another. Alternatively, a lengthy process step may take place between first and second times for determining the level of contamination from a particular process. Typically, scanning does not extend to the very edge of a wafer due to the fact that the edges of even perfect wafers scatter a considerable amount of light in the light collection system. An excluded zone demarcated by dashed curve 47 separates the central measured area of the wafer from the wafer edge. The excluded zone forms an annular ring extending up to about 10 millimeters from the edge.

In FIG. 2, during the first scan at the first time, particles 49, 51, 53, etc., hereafter referred to as "first particles" are detected. In FIG. 3, during a later scan at a second time, particles 57, 59, 61, 63, 65, etc., hereafter referred to as "second particles" are detected. Some of the first and second particles may be the same, but may not have the same measured positions due to possible movement, either translation or rotation, of the wafer between the two scans. Further, the same particles may not have the same measured light scattering intensity due to the somewhat variable nature of parameters affecting scattering. These variables include, but are not limited to, a lack of overlap of two consecutive scans, variable illumination angle, variable focus, laser power fluctuation, electronic or background noise, photon statistics, and finite sampling density. Other particles may not be the same, but instead be added or removed between scans. While we refer here to particles, other defects such as scratches, pits and the like may also be detected and analyzed together with particles and other contamination with or without distinction in kind.

In FIG. 2, three first particles 49, 51 and 53 are selected from computer memory and define a first triangle 55. Alternatively, four or more particles may be selected to form some other polygon. The first particles selected have a measured light scattering intensity which is substantially above the predetermined collection threshold intensity, so that unless the particles are removed, the particles will be nearly always detected during the second scan. Preferably, these particles are selected from a set containing those 3 to 10 particles with the largest light scattering intensity. The triangle 55 or other polygon defined by the selected particles is characterized by an area and a perimeter. For any two particles with measured X- and Y-positions of $(X_1, Y_1)$ and $(X_2, Y_2)$, the distance d between them is given by:

$$d^2 + (X_2 - X_1)^2 + (Y_2 - Y_1)^2$$

The perimeter P of the triangle 55 is then given by:

$P = a + b + c$, where a, b and c are the three distances between respective pairs of selected particles.

Likewise, the area A is given by $$A = [s(s-a)(s-b)(s-c)]^{\frac{1}{2}}, \text{ where } s = P/2.$$

Alternatively, the area may be determined directly from the measured positions $(X_1, Y_1)$, $(X_2, Y_2)$ and $(X_3, Y_3)$ by:

$$A = \tfrac{1}{2}(X_1Y_2 - X_2Y_1 + X_2Y_3 + X_3Y_2 - X_3Y_1 - X_1Y_3).$$

For the most accurate transformation results, the area of the triangle 55 is preferably as large as possible. Also, although we are using the perimeter and area of the triangle as the characteristic parameters, other parameters may be used, such as the individual distances between pairs of selected particles and angles formed by the particles. In any case, the technique relies only on the interparticle distances and not on the positions of particles relative to a flat edge or other fixed point of the wafer.

In FIG. 3, after first particles 49, 51 and 53 have been selected to form first triangle 55, second particles are selected as candidates for each of the selected first particles. Each candidate second particle has a light scattering intensity within a predetermined range of intensities around the light scattering intensity of the selected first particle for which it is a candidate and also an estimated radius. For example, second particles 57 and 63 may have a scattering intensity which falls with the range for first particle 49. Particles 57 and 63 are then selected as candidates for first particle 49, i.e. one of these candidate particles may be the same particle as first particle 49. Similarly, candidates are selected for the other selected first particles 51 and 53. Second particles may be candidates for more than one selected first particle. A first particle in FIG. 2 may have one or more candidate second particles in FIG. 3. If no candidates are found for a first particle, another first particle is selected and the perimeter and area for the new triangle are computed. Typically, the scattering intensity for candidate particles falls between 0.5 and 1.5 times the scattering intensity of the corresponding first particle.

After selecting candidate second particles, variants of the first triangle 55 are formed from the candidates. For example, triangle 67, indicated by dashed lines in FIG. 3, is formed from second particles 63, 65 and 57, candidates for first particles 49, 51 and 53 respectively. Another variant triangle 69, indicated by solid lines in FIG. 3, is formed from second particles 57, 59 and 61, candidates for first particles 49, 51 and 53 respectively. Each variant triangle or other polygon is characterized by a perimeter and area. Particles 57, 59 and 61 forming the variant 69 with the perimeter and area closest to within a specified percent of that of first triangle 55 are identified as being the same particles as the respective selected first particles 49, 51 and 53 that form first triangle 55.

In the event only one or two particles are detected on a wafer, particles seen in different scans are matched by using the distance from the rough center of the wafer as a reference. Particles in different scans whose distances from the wafer center are closest, within a specified percentage, are considered to be the same particle. In the event no particles are detected on a wafer, no matching is required.

Once these first and second particles 49 and 57, 51 and 59, and 53 and 61 are matched, transformations which map one set of measured positions onto the other corresponding set of measured positions are calculated. If $(X_1, Y_1)$ and $(X_1', Y_1')$ are the measured positions of particle 49 and 57 at respective first and second times then $$X_1' = (\cos\theta)(X_1 - h) + (\sin\theta)(Y_1 - k)$$

$$Y_1' = -(\sin\theta)(X_1 - h) + (\cos\theta)(Y_1 - k)$$

where h and k are the desired linear displacements and $\theta$ is a rotational displacement. Two other pairs of equations may be obtained from the measured positions at respective first and second times of the other pairs of same particles 51 and 59, and 53 and 61. The equations may be solved simultaneously using known matrix algebra techniques to obtain h, k and $\theta$, and thus the desired transformation and inverse transformation.

Once the transformations are known, they can be applied to the positions of particles on one scan to find the corresponding particle positions on a subsequent scan or vice-versa. An area around each corresponding position is then examined for the presence of a particle. For example, area 73 in FIG. 2 containing a first particle 71 corresponds to an area 75 in FIG. 3 containing second particle 77. Accordingly, first and second particles 71 and 77, match, i.e. are identified as being the same particle. In FIG. 2, an area 79 contains a first particle, but the corresponding second area 81 in FIG. 3 contains no particle. Accordingly, the particle in area 79 is considered to have been removed in the interval between the two scans. In FIG. 3, a second area 83 contains a second particle, but the corresponding first area 85 in FIG. 2 contains no particle. Accordingly, the particle in area 83 is considered to have been added in the interval between the first and second scans. Finally, in FIG. 2 an area 87 contains one particle 88, while the corresponding area 89 in FIG. 3 contains two particles 91 and 93. In the case of plural particles in an area, the particle whose light scattering intensity is closest to that of particle 88 is considered to match. Alternatively, the measured positions of the plural particles may be used as a matching criteria instead of scattering intensity.

The mapping technique may be used to synthesize the results from several scans. For example, four scans may be taken of a wafer before introducing the wafer to a process step and another four scans may be taken after the process step. By using the mapping technique to identify identical particles in the four "before" scans, the measured scattering intensities of each particle can be averaged to obtain a mean scattering intensity representative of the particle. Likewise, the four "after" scan intensities can be averaged to obtain a mean for each particle found after wafer processing. The "before" and "after" maps can then be compared as described elsewhere but using the average intensity values of the particles.

Figure 4:
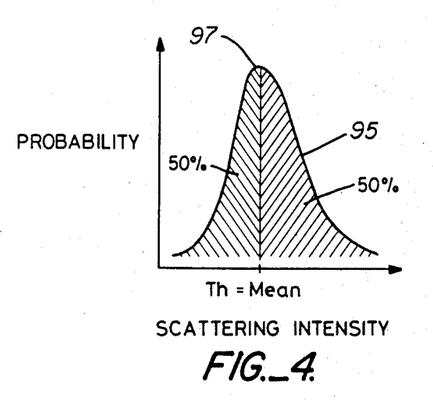
FIGS. 4 and 5 are graphs of probability of observing a particle at a particular scattering intensity vs. scattering intensity.
Figure 5:
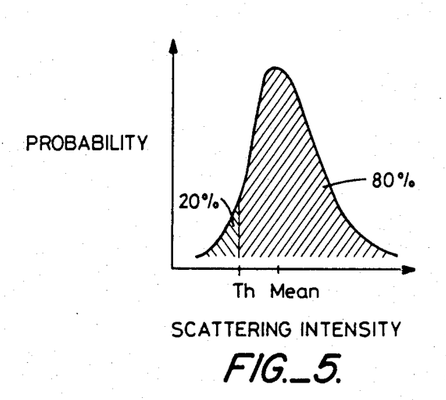

So far we have not considered the examination of corresponding areas for matching particles with respect to any light scattering threshold intensity. With reference to FIG. 4, particles do not usually scatter a fixed amount of light, but due to many random elements in the manner of illuminating the particle, background noise levels, photon statistics and the like the measured level of light scattering may vary from scan to scan. The probability of observing any given scattering intensity is given by the curve 95 which is a normalized histogram of particle observations. This curve has a maximum probability of occurrence 97. The curve falls off for higher and lower scattering intensities, so that approximately 50% of the observed light intensities for a given particle is to right of the peak, i.e. higher intensities, and approximately 50% of the observed light intensities is to the left of the peak. Accordingly, a particle whose mean light scattering intensity is equal to the threshold intensity will be observed in only 50% of the scans. In FIG. 5, on the other hand, a large particle with a mean light scattering intensity which is greater than the threshold intensity will be observed in greater than 50% of the scans, here about 80%. The mean scattering intensity is an indication of the approximate size of a particle, with larger particles having greater scattering intensity on the average than smaller particles.

Figure 6:
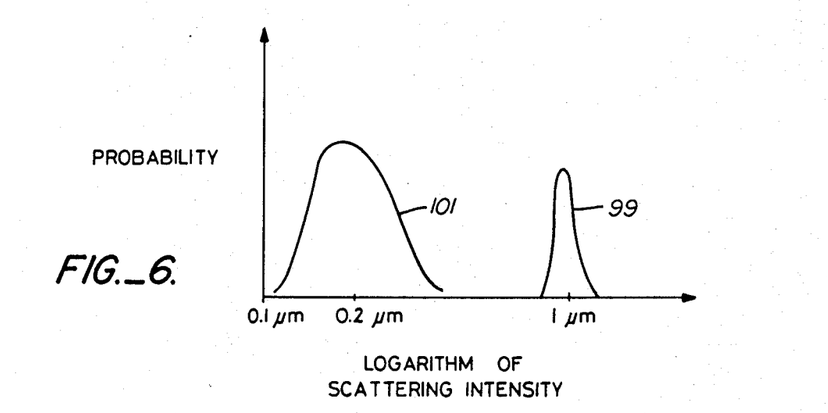
FIG. 6 is a graph of probability vs. the logarithm of the scattering intensity showing the spread of observed intensities for particles of various sizes.

The actual measured scattering intensity dances around statistically, and individual particles whose mean scattering intensity is near the threshold intensity are sometimes detected and sometimes not detected depending on the scan. For very small particles with levels of scattered light near the limits of machine detectability, photon statistical variations and optical background noise tend to be relatively large, and the measured scattering intensity is relatively more variable. For example, in FIG. 6, a particle 99 having a size of about 1 $\mu$m and a scattering cross-section of 0.94 $\mu m^2$ exhibits a standard deviation of about 0.07 $\mu$m, i.e. approximately 7% of the mean scattering intensity. A smaller particle 101 having a size of about 0.2 $\mu$m and a scattering cross-section of 0.06 $\mu m^2$ exhibits a standard deviation of about 0.002 $\mu m^2$, i.e. approximately 35% of the mean scattering intensity. The wide variation in measurements can mean that the particle count of added or removed particles can vary widely if the threshold intensity is set too low.

Figure 7:
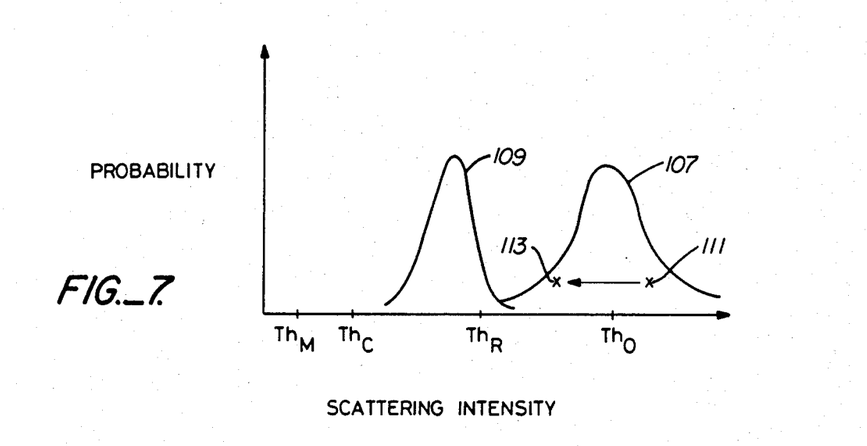
FIG. 7 is a graph of probability vs. scattering intensity illustrating the threshold consideration of the method of the present invention.

In FIG. 7, the method of the present invention provides a solution to this problem. The technique produces results which are substantially independent of particle size and works for all histograms. In this method, particles are detected above a collection threshold intensity $Th_C$ and their position and scattering intensity information stored in computer memory. But only particles with a scattering intensity above a display or threshold intensity $Th_D$ are examined for corresponding particles in another scan. If no matching particle is found using display threshold $Th_D$, the areas described in FIGS. 2 and 3 are reexamined at a reduced threshold intensity $Th_R$. The display threshold $Th_D$ is typically the same as that used for the map-to-map transformation calculations discussed above, in which case it may also be called the map-to-map threshold. Since particles with scattering intensities below the reduced threshold $Th_R$ are not examined, the collection threshold intensity $Th_C$ is usually equal to the reduced threshold $Th_R$. However, since users occasionally analyze the same set of data for several different display thresholds $Th_D$, the collection threshold $Th_C$ can be set substantially lower than both the reduced threshold $Th_R$ and the display threshold $Th_D$. The collection threshold $Th_C$ may be fixed as low as the limits of detectability for the particle detection apparatus, i.e. the machine threshold $Th_M$. Typical machine thresholds for particle detectors like that in FIG. 1 are about 0.2 $\mu$m. The reduced threshold intensity $Th_R$ is lower than the display threshold intensity $Th_D$ by a predetermined amount. While this amount may be fixed, it is usually variable. The ratio of the reduced threshold $Th_R$ to the display threshold $Th_D$ is a value between 0 and 1, where a ratio of one represents prior particle detection methods, and in the present invention is preferably set substantially less than 1. The reduced threshold is typically selected so that the reduction corresponds to about one-half the the display threshold. In the remainder of this specification, reference will be made to only two thresholds, a mapping or display threshold $Th_D$, and a reduced threshold $Th_R$, usually equal to the collection threshold.

In FIG. 7, a particle represented by probability curve 107 has a size or mean scattering intensity which is near the user selected display threshold intensity $Th_D$. In one scan, the particle may be detected with a scattering intensity indicated by mark 111, while in another scan, the particle may have a scattering intensity below the display threshold $Th_D$, as indicated by mark 113. When examining an area for particles above the display threshold $Th_D$, particle 107 will sometimes be detected and sometimes will not be detected. When the occurrence of particle 107 is not detected, as for the scan indicated by mark 113, reducing the threshold intensity to $Th_R$ and reexamining the area enables the particle to be observed. Note that examining all particles at the reduced threshold $Th_R$ would not solve the problem, since the problem would then be repeated for smaller particles, such as particle 109. However, by examining for particles at the display threshold $Th_D$ and then reducing the threshold only when no particle is found, particles 107 near the display threshold $Th_D$ can be consistently detected, while reducing the probability of detecting smaller particles 109.

Figure 8:
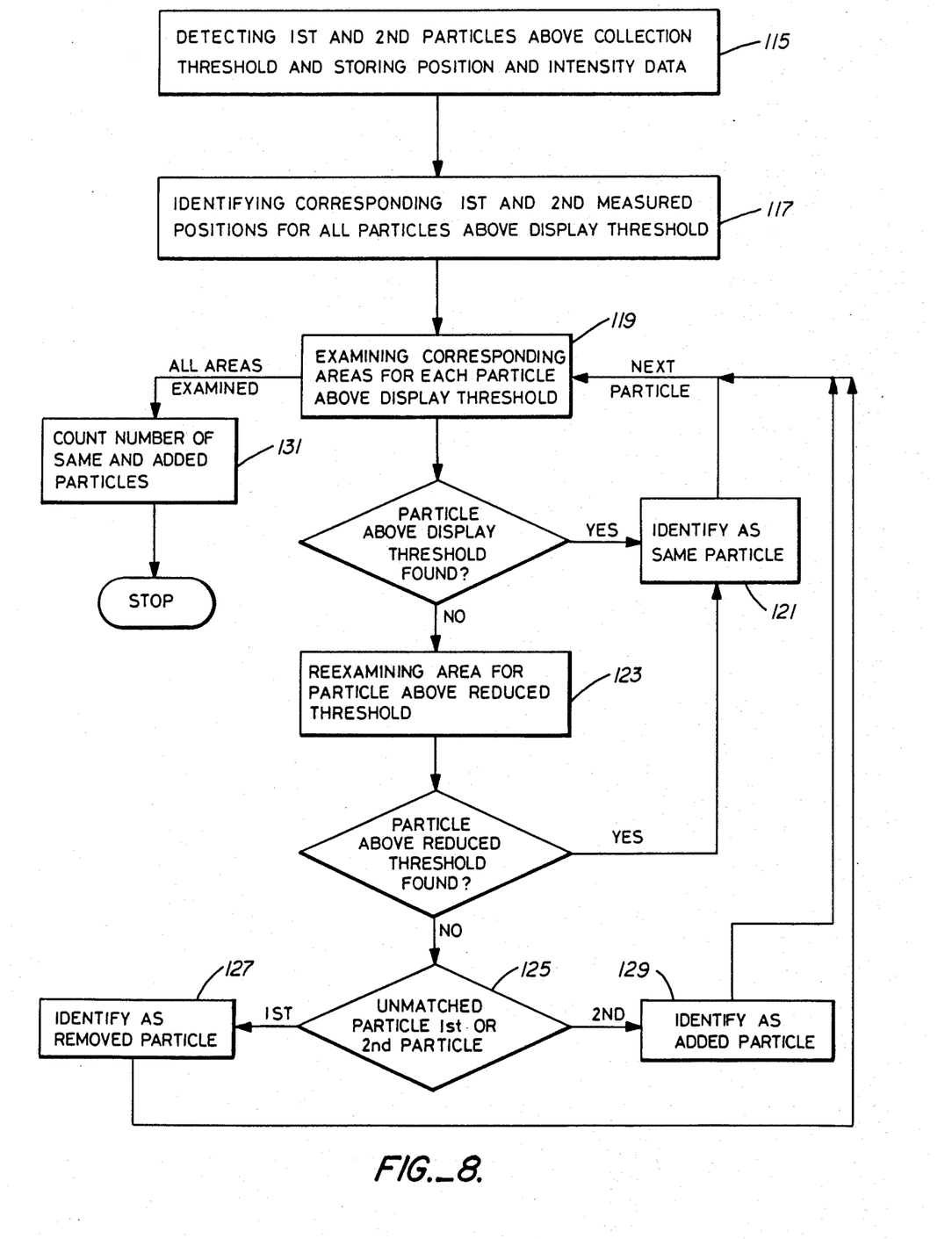
FIG. 8 is a flow diagram of the method of the present invention.

With reference to FIG. 8, the method of the present invention comprises first detecting 115 first and second particles at first and second times which have a measured light scattering intensity above a predetermined collection threshold intensity, and storing the measured position and scattering intensity data for each detected particle in computer memory. Next, one identifies 117 the corresponding first and second measured positions for at least all particles with a scattering intensity above a user specified display threshold intensity. This identification step 117 is preferably performed as described above with reference to FIGS. 2 and 3, i.e. determining a transformation that maps first particle positions onto corresponding positions of the second scan, and vice versa.

Once corresponding positions have been identified, one examines 119 corresponding areas for each particle with a scattering intensity above the display threshold. If a particle is found in the area corresponding to a particular particle, these two particle detections are identified 121 as the same particle. If no particles are found in the corresponding area, the threshold is reduced and the area is reexamined 123 for particles having a scattering intensity above the reduced threshold. Again if a particle is found it is identified as being the same as the corresponding particle. If no particle is found in the corresponding area above the reduced threshold, then the particle being analyzed is an unmatched particle 125. If it is an unmatched first particle, detected at the first time during the first scan, but not detected at the second time during the second scan, it is identified as a removed particle. Likewise, if it is an unmatched second particle, it is identified as an added particle. Once all areas corresponding to particles with scattering intensities above the display threshold have been examined, the total number of particles identified as the same, added or removed are counted 131. The distribution of these particles may also be displayed, along with a histogram of the distribution of the mean observed scattering intensities of the particle.

The just described dual threshold method is capable of a more repeatable particle count in a few scans than methods using a single threshold and averaging results from a much larger number of scans. Further, by synthesizing the results of several scans before and after a process step in combination with a dual threshold, an accurate count of particles added or removed by a process step is obtained. While the invention has been described in terms of particles on wafer surfaces, other surfaces may also be examined and defects other than particles may also be counted. Further, the method can be extended to the analysis of other forms of detection, such as the position and intensities of stars imaged on a photographic plate. In such an instance, two plates taken at different times can be compared to find "particles", i.e. images of stars, planets, comets, etc. which have moved during the time interval. Accordingly, the term "particle" is construed to include any detected point, distinct object, or event with measurable position.

We claim:

1. A method of matching particles detected on a surface at consecutive times comprising, detecting first particles on a surface at a first time, each first particle being characterized by a first measured position and by a first light scattering intensity reaching a photodetector that is above a predetermined collection threshold intensity, storing said position and light scattering intensity information for each first particle in a computer memory, detecting second particles on said surface at a second time, at least some of said second particles being the same as at least some of said first particles, each second particle being characterized by a second measured position and by a second light scattering intensity reaching a photodetector that is above said predetermined collection threshold intensity, storing said position and light scattering intensity information for each second particle in a computer memory, selecting from computer memory three or more first particles with light scattering intensities that are substantially above said threshold intensity, said selected first particles defining a first polygon characterized by a perimeter and an area, selecting from computer memory candidate second particles for each of said selected first particles, each candidate second particle having a light scattering intensity within a predetermined range of intensities around the light scattering intensity of said selected first particle for which said second particle is a candidate, forming variants of said first polygon with said candidate second particles, said variants characterized by a perimeter and area, candidate second particles forming the variant determined to have the perimeter and area closest to those of said first polygon to within a specified percentage being identified as the same as the corresponding selected first particles that form said first polygon, and calculating from the first and second measured positions of said identified same particles the translation and rotation transformations which map one of said first and second measured positions into the other of said first and second measured positions.

2. The method of claim 1 wherein three first particles are selected, said first polygon being a triangle.

3. The method of claim 1 wherein said predetermined range is from one-half of said light scattering intensity of a selected first particle to three-halves of said light scattering intensity of said selected first particle.

4. The method of claim 1 wherein said first particles defining said first polygon are selected from a set of predetermined size containing those first particles with the largest light scattering intensity.

5. The method of claim 1 further comprising,
applying said transformations to at least one set of said first and second measured positions so as to obtain a set of corresponding first and second measured positions,
examining corresponding first and second areas around each of said corresponding first and second positions, a single particle within both corresponding areas being identified as the same particle.

6. The method of claim 5 wherein a single particle within only the first of said corresponding areas is determined to have been removed, and a single particle within only the second of said corresponding areas is determined to have been added.

7. The method of claim 5 wherein plural particles are found to be within at least one of said corresponding first and second areas, pairs of particles closest in light scattering intensity being identified as the same particles.

8. A method of matching particles detected on a surface at consecutive times comprising,
(a) detecting first particles on a surface at a first time, each first particle being characterized by a first measured position and by a first light scattering intensity reaching a photodetector that is above a collection threshold intensity,
(b) storing said position and light scattering intensity information for each first particle in computer memory,
(c) detecting second particles on a surface at a second time, each second particle being characterized by a second measured position and by a second light scattering intensity reaching a photodetector that is above said collection threshold intensity,
(d) storing said position and light scattering intensity information for each second particle in computer memory,
(e) identifying corresponding first and second measured positions,
(f) examining corresponding first and second areas around the measured position and the identified corresponding position of each first and second particle having a light scattering intensity above a predetermined display threshold intensity, said display threshold intensity being higher than said collection threshold intensity, a single particle within each of the corresponding first and second areas, both having light scattering intensities above said display threshold intensity, being identified as the same particle, and
(g) whenever a particle having a light scattering intensity above said display threshold intensity is found within only one of said corresponding first and second areas, reexamining the other of said corresponding areas for a detected particle having a light scattering intensity that is reduced from said display threshold intensity by a predetermined amount, (i) a particle detected within said one area with a light scattering intensity above said display threshold and a particle detected within said corresponding other area with an intensity above said reduced threshold being identified as the same particle, (ii) a first particle detected within said first area with a light scattering intensity above said display threshold and no particle detected within said corresponding second area with an intensity above said reduced threshold being considered removed, and (iii) a second particle detected within said second area with a light scattering intensity above said display threshold and no particle detected within said corresponding first area with an intensity above said reduced threshold being considered added.

9. The method of claim 8 wherein said reduced threshold intensity is a predetermined fraction of the value of the display threshold intensity.

10. The method of claim 8 further comprising counting the number of first and second particles identified as being the same.

11. The method of claim 8 further comprising counting the number of added particles.

12. The method of claim 8 wherein identifying corresponding first and second measured positions comprises,
selecting from computer memory three first particles with light scattering intensitiies substantially above said collection threshold intensity, said selected first particles defining a first triangle characterized by a perimeter and an area,
selecting from computer memory candidate second particles for each of said selected first particles, each candidate second particle having a light scattering intensity within a predetermined range of intensities around the light scattering intensity of the selected first particle for which said second particle is a candidate,
forming variants of said first triangle with said candidate second particles, said variants characterized by a perimeter and an area, candidate second particles forming the variant determined to have the perimeter and area closest to the perimeter and area of said first triangle being identified as the same particles as the corresponding selected first particles,
calculating from the measured first and second positions of said identified same particles the transformations for mapping each of said sets of measured first and second positions into the other set, and
applying said transformations to each first and second measured positions of particles with scattering intensities above said display threshold intensity.

13. A method comprising,
(a) detecting with a measuring instrument at least one first event in a first set of measurements, each first event characterized by an event location and by a parameter measured by said instrument that is above a collection threshold,
(b) detecting with said instrument at least one second event in a second set of measurements, each second event characterized by an event location and by a parameter measured by said instrument that is above said collection threshold,
(c) for each event in one set of measurements with a measured parameter that is above a display threshold, examining an event location in the other set of measurements that corresponds to the event location of said event, an event detected at the corresponding event location in the other set of measurements with a measured parameter that is above said display threshold being determined to match the event in the one set of measurements, and (d) whenever an event with a measured parameter that is above said display threshold is absent from said corresponding event location, reexamining said corresponding event location for events with a measured parameter above a reduced threshold, said reduced threshold being below said display threshold by a predetermined amount, an event detected at said corresponding event location in the other set of measurements with a measured parameter above said reduced threshold being determined to match the event in the one set of measurements, and (e) whenever an event with a measured parameter that is above said reduced threshold is absent from said corresponding event location, a first event being determined to be old, and a second event being determined to be new.

14. The method of claim 13 wherein said event locations are measured spatial positions together with a predetermined surrounding area.

15. The method of claim 13 wherein said reduced threshold is one-half of said display threshold.

16. The method of claim 13 further comprising counting the number of events being determined to match.

17. The method of claim 13 further comprising displaying the events being determined to match according to event locations.

18. The method of claim 13 further comprising counting the number of new events.

19. The method of claim 13 further comprising displaying the new events according to event location.

* * * * *